(12) United States Patent
Lantsberg et al.

(10) Patent No.: US 8,302,239 B2
(45) Date of Patent: Nov. 6, 2012

(54) ORBITAL ELECTRIC TOOTHBRUSH

(76) Inventors: Igor Lantsberg, Beachwood, OH (US);
Gregory Greenspan, Solon, OH (US);
Alexander Greenspan, Solon, OH (US);
Gene Alter, Chagrin Falls, OH (US)

( * ) Notice: Subject to any disclaimer, the term of this patent is extended or adjusted under 35 U.S.C. 154(b) by 661 days.

(21) Appl. No.: 12/501,151

(22) Filed: Jul. 10, 2009

(65) Prior Publication Data
US 2011/0005013 A1    Jan. 13, 2011

(51) Int. Cl.
*A46B 13/02* (2006.01)
(52) U.S. Cl. .......................... 15/22.1; 15/22.4
(58) Field of Classification Search ............ 15/22.1, 15/22.4, 167.1, 201
See application file for complete search history.

(56) References Cited

U.S. PATENT DOCUMENTS

| 2,263,802 | A | * | 11/1941 | Grusin | 15/110 |
| 5,398,366 | A | * | 3/1995 | Bradley | 15/167.1 |
| 5,423,102 | A | * | 6/1995 | Madison | 15/22.2 |
| 5,862,558 | A | * | 1/1999 | Hilfinger et al. | 15/28 |
| 7,251,849 | B2 | * | 8/2007 | Moskovich et al. | 15/28 |
| 2006/0010623 | A1 | * | 1/2006 | Crossman et al. | 15/22.1 |

FOREIGN PATENT DOCUMENTS
WO           98/11843      *   3/1998

* cited by examiner

*Primary Examiner* — Randall Chin
(74) *Attorney, Agent, or Firm* — McDonald Hopkins LLC

(57) ABSTRACT

An electric toothbrush with improved brush head motion is provided. The electric toothbrush includes a head comprising a fixed base having a concave portion, and a brush head having a convex portion. The convex brush head nests within the concave base to allow for rotational and tilting movement of the brush head relative to the base. The brush head movement may be driven by a motor housed within the toothbrush.

17 Claims, 8 Drawing Sheets

US 8,302,239 B2

ORBITAL ELECTRIC TOOTHBRUSH

FIELD OF THE INVENTION

The present invention relates generally to electric toothbrushes and more particularly, to an electric toothbrush with improved circular orbital motion.

BACKGROUND OF THE INVENTION

Toothbrushes provide many oral hygiene benefits, including removal of plaque, food, and debris to help avoid tooth decay and disease. They remove stained pellicle from the surface of each tooth to help whiten the teeth. The bristles combined with the brushing motion also massage the gingival tissue for stimulation and increased tissue health.

Powered toothbrushes have been available for some time. Powered toothbrushes have advantages over manual (non-powered) toothbrushes in that they impart movement to the bristles at much higher speeds than possible manually. They also may impart different types and directions of motion. These motions, in combination with manual movement of the toothbrush by the user, generally provides superior cleaning than manual toothbrushes. Typically, powered toothbrushes are powered by disposable or rechargeable batteries that power an electric motor, which in turn drives the toothbrush head.

Known powered toothbrushes include a brush head with a bristle carrier portion that rotates, oscillates or vibrates in some manner so as to clean the teeth. The bristles, which typically comprise bristle tufts, are generally uniform with one end fixed into the bristle carrier portion and the other end free to contact the surface of the teeth while brushing. The free ends of the various tufts present a surface envelope that is capable of some deformation when the bristles bend. When in contact with the surface to be brushed, the bristles may deform so that the surface envelope tends to conform to the complex surface of the teeth. Human teeth generally lie in a "C" shaped curve within the upper and lower jaw, and each row of teeth consequently has a convex outer curve and a concave inner curve. Individual teeth often have extremely complex surfaces, with areas that may be flat concave, or convex. The more precise conformation between the bristles and the tooth surface, the more effective the toothbrush may be in cleaning, whitening and/or stimulating.

Conventional electric toothbrushes provide limited bristle movement in one or two dimensions. For example, known toothbrushes may include circular or cylindrical brush heads that move rotationally in a clockwise and counterclockwise reciprocating movement. Additionally, other known toothbrushes provide up and down bristle movement parallel to the toothbrush body, or back and forth movement perpendicular to the toothbrush body. While these designs enhance traditional manual brushing, they are limited in the engagement between the bristles and the teeth. Moreover, two dimensional movement of the bristles may cause pinching of the gums, or other discomfort or irritation. Therefore, an electric toothbrush with improved brush head movement is needed in the art to provide better and more comfortable teeth cleaning.

SUMMARY OF INVENTION

An electronic toothbrush with improved movement of the brush head is provided. The electric toothbrush includes a head connected to a handle. The head comprises a base having a concave portion, and a brush head having a convex portion. The convex portion of the brush head is configured to nest within the concave portion of the base to allow rotational and tilting movement of the brush head with respect to the base. The toothbrush may include a motor to drive the movement of the brush head. The motor may drive a wheel connected to the brush head.

DESCRIPTION OF THE DRAWINGS

In the accompanying drawings, which are incorporated in and constitute a part of this specification, embodiments of the invention are illustrated, which, together with a general description of the invention given above and the detailed description given below, serve to illustrate the principles of this invention. The drawings and detailed description are not intended to and do not limit the scope of the invention or the claims in any way. Instead, the drawings and detailed description only describe embodiments of the invention, and other embodiments of the invention not described are encompassed by the claims.

DETAILED DESCRIPTION

The Detailed Description of the Invention merely describes preferred embodiments of the invention and is not intended to limit the scope of the claims in any way. Indeed, the invention as described by the claims is broader than and unlimited by the preferred embodiments, and the terms in the claims have their full ordinary meaning.

Figure 1:
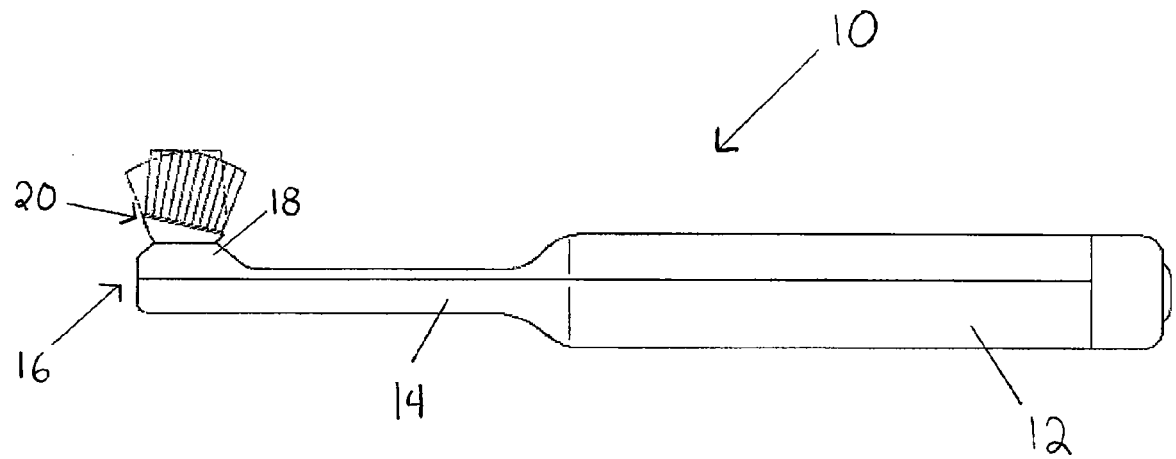
FIG. 1 illustrates a side profile view of an electric toothbrush.
Figure 2:
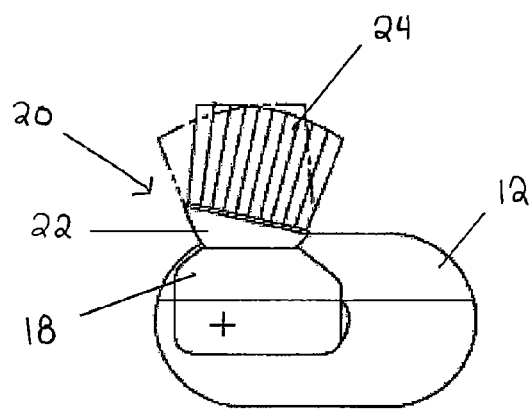
FIG. 2 illustrates a top view of an electric toothbrush having a powered brush head.

An electronic toothbrush 10 with improved brush head movement is provided. With reference to FIGS. 1 through 4, the electronic toothbrush 10 generally includes a handle 12 located at a proximal end of the toothbrush 10, a neck 14 extending from the handle 12, and a head 16 connected to the neck 14 and located at a distal end of the toothbrush 10. In other words, as shown in FIG. 1, the neck 14 extends between the handle 12 and the head 16 to interconnect the head 16 and the handle 12. The handle 12, neck 14 and head 16 may be integrally formed as a single unitary member. Alternatively, the handle 12, neck 14, and head 16 may each be individual members, detachable from the rest of the toothbrush 10 to permit cleaning and servicing of the toothbrush 10, as well as interchanging of components. It will be appreciated that the shape and design of the handle 12, neck 14 and head 16 illustrated in the drawings are merely exemplary in nature.

Preferably, the shape of the handle 12 and neck 14 will be ergonomically efficient to allow a user to easily use the toothbrush 10. However, the handle 12, neck 14 and head 16 may be any size or shape.

The head 16 may include a base 18 and a brush head 20. The base 18 may be a fixed portion connected to the neck 14. The brush head may be movably connected to the base 18. The brush head 20 may comprise a bristle carrier 22 and a plurality of bristles 24 coupled to the bristle carrier 22. As used herein, the term "bristles" generally defines tooth care elements and includes any type of structure that is commonly used or is suitable for use in providing oral health benefits (e.g., tooth cleaning, tooth polishing, tooth whitening, etc.) by making contact with surfaces of the teeth, gums, and surrounding areas. Such bristles include, but are not limited to individual bristle strands or tufts of bristles, formed to have any different number of shapes and sizes. Moreover, while the bristles may be arranged such that they are generally perpendicular to the surface of the toothbrush 10, some or all of the bristles may be configured at varying angles with respect to the face of the toothbrush 10.

The brush head 20 may move with respect to the base 18. Specifically, as described in further detail below, the engagement between the brush head 20 and the base 18 may permit rotational and tilting movement of the brush head 20 with respect to the base 18. Rotational movement may include rotation of the brush head 20 or a portion of the brush head 20 with respect to the base 18. Tilting movement may include angular movement of the brush head 20 with respect to the base 18. Thus, the rotational and tilting movement enables the bristles 24 to travel in three dimensions, namely rotation of the bristles 24 within the plane approximately parallel to the face of the toothbrush 10, and angular tilting movement of the bristles 24 towards and away from the surface of the teeth.

To facilitate rotational and tilting movement, the base 18 may include an opening 26 of similar size and shape to the bristle carrier 22. For example, the bristle carrier 22 may be convex in shape, such as semi-spherical shaped. Likewise, the base 18 may include a concave shaped opening 26 to receive the bristle carrier 22. The convex bristle carrier 22 may nest within the concave opening 26 in the base 18, thereby enabling both tilting movement of the brush head 20 with respect to the base 18, and rotational movement of the brush head 20 with respect to the base 18.

Figure 3:
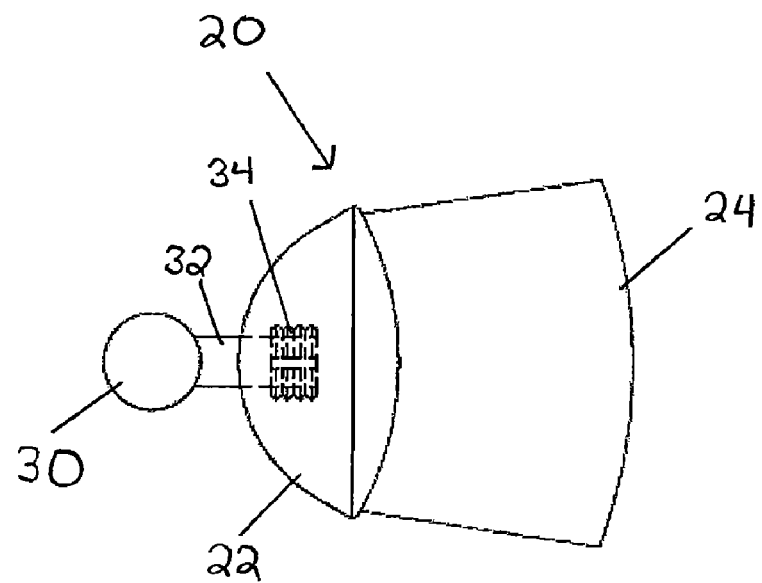
FIG. 3 illustrates side view of a brush head.
Figure 4:
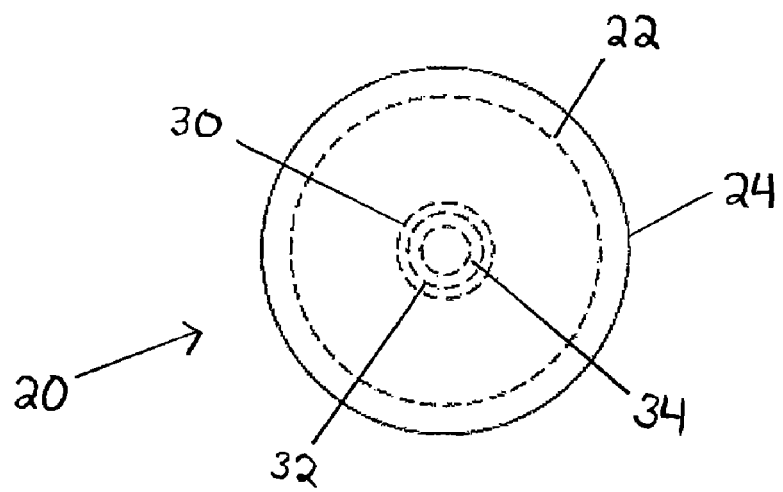
FIG. 4 illustrates a front view of a brush head.
Figure 5:
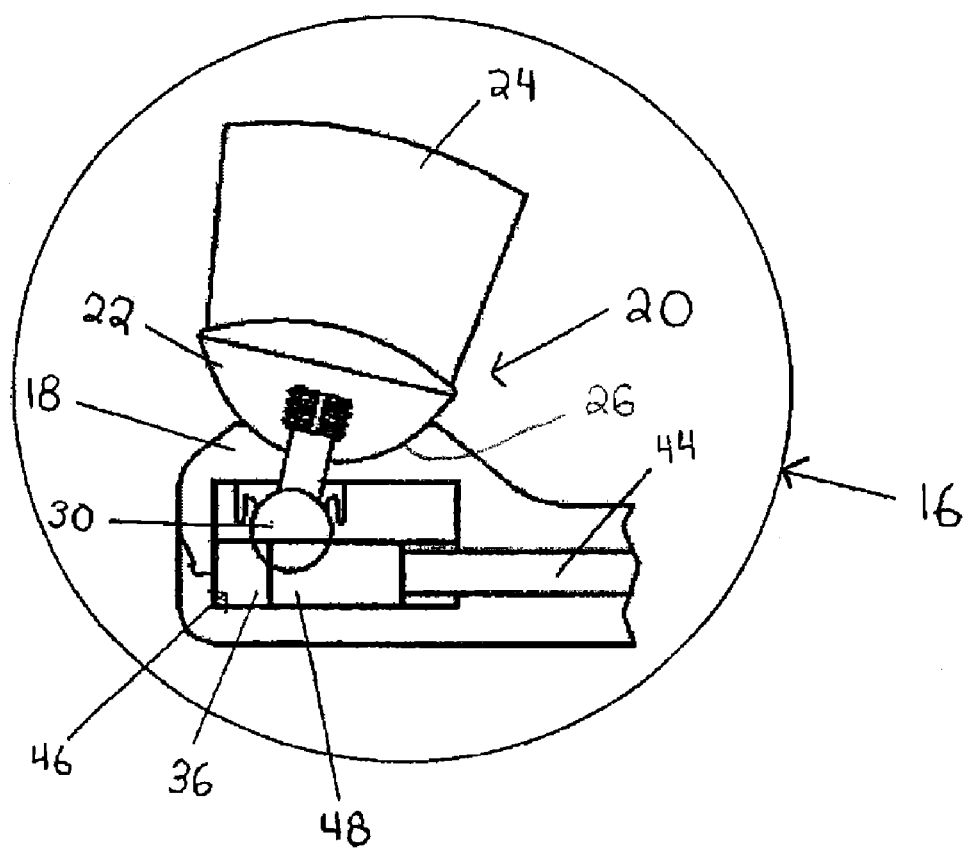
FIG. 5 illustrates a cross-sectional side view of an electric toothbrush with an enhanced view of the toothbrush head.

The brush head 20 may connect to the head 18 by way of a joint, such as a ball and socket joint. As shown in FIGS. 3 and 5, the brush head 20 may include a ball 30 joined to a screw 32. The screw may connect to the bristle carrier 22 such that the ball 30 is spaced a distance from the convex surface of the bristle carrier 22. The screw 32 may be removably connected to the bristle carrier 22. For example, the screw 32 may include a threaded portion 34 to engage a threaded opening in the bristle carrier 22. Alternatively, the screw may be integrally formed with the bristle carrier 22. While the brush head 20 is described as having a ball 30 and screw 32 connection to the head 18, it will be appreciated that the brush head 20 may include alternative connections means, such as a barbed ball joint or other connecting devices known in the art.

Figure 6:
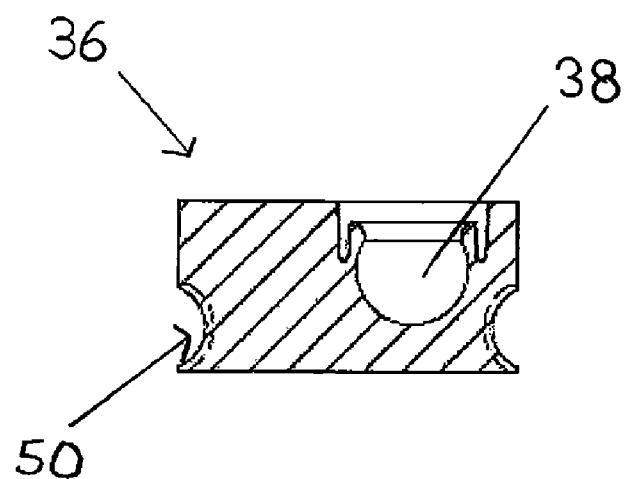
FIG. 6 illustrates a wheel configured to engage a worm.
Figure 7:
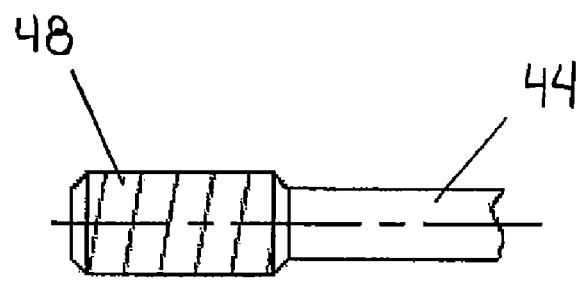
FIG. 7 illustrates a threaded worm.

With reference to FIGS. 5 and 6, the head 16 may include a wheel 36 located inside the head 16. The wheel 36 may be positioned beneath the base 18, such that the base 18 is located between the wheel 36 and the bristle carrier 22. The wheel may include a socket 38 sized and shaped similar to the ball 30. The ball 30 may fit into the socket 38 to allow rotational movement of the ball 30 within the socket 36, yet prevent the ball 30 from being removed from the socket 38. The base 18 may include an opening to allow the screw 32 to extend therethrough.

The brush head 20 may be removable from the head 16 to permit cleaning and servicing of the toothbrush 10 or replacement of the brush head 20. For example, the ball 30 may be removable from the socket 38 to allow the brush head 20, ball 30 and screw 32 to be removed from the head. They brush head 20 may also be removed from the head by unscrewing the bristle carrier 22 from the screw 32.

The wheel 36 may be configured to impart rotational and tilting movement on the brush head 20. For example, the wheel 36 may be rotatable about its central axis. The socket 38 may be located off-center, away from the central axis. Further, the central axis of the wheel 36 may be aligned with the opening in the base 18 to permit the screw 32 to extend therethrough. As illustrated in FIG. 5, the screw 32 extends from the ball 30, located in the off-center socket 38, to the bristle carrier 22 at an angle less than 90 degrees relative to the face of the wheel 36. As the wheel 36 is rotated about its central axis, the rotational movement is transferred to the brush head 20 by way of the ball 30 and screw 32. Moreover, the angular arrangement of the screw 32 provides angular tilting of the brush head 20 as it rotates.

The wheel 36 may be driven by a motor, such as an electric direct current ("DC") motor 40. The motor 40 may be housed within the handle 12, as shown in FIG. 5. Alternatively, the motor 40 may be housed within the neck 14 or head 16. The motor 40 may be powered by an electrical power source such as batteries 42. The handle 12 may include a compartment or housing for containing both the motor 40 and batteries 42. In an embodiment, the batteries 42 are rechargeable batteries. The handle may include a contact, formed out of a conductive material, in electrical connection with the batteries 42 to allow the batteries 42 to be recharged without removing them from the housing. While the toothbrush 10 is described herein as utilizing battery power, it will be appreciated that the toothbrush 10 may receive power from an electrical outlet, or may any other source known in the art.

The motor 40 includes a rotatable shaft 44 to drive the wheel 36. The shaft 44 extends along the length of the neck and is coupled to the wheel 36. In an embodiment, illustrated in FIGS. 5 through 9, the shaft 44 is coupled to the wheel 36 by way of a worm gear 46. The worm gear 46 includes a worm 48 or threaded screw attached at the end of the shaft 44 opposite the motor 40. The threads of the worm 48 engage corresponding teeth or gears on the wheel 36. Specifically, the wheel 36 may include a recessed portion 50 to receive the threaded worm 48. As the motor 40 rotates the shaft 44, the worm 48 spins about its axis. The threads of the worm 48 engage the teeth or gears of the wheel 36 to rotate the wheel 36 about its central axis. As previously described, the rotating wheel 36 and socket 38 then imparts rotational and tilting movement to the brush head 20.

Figure 8:
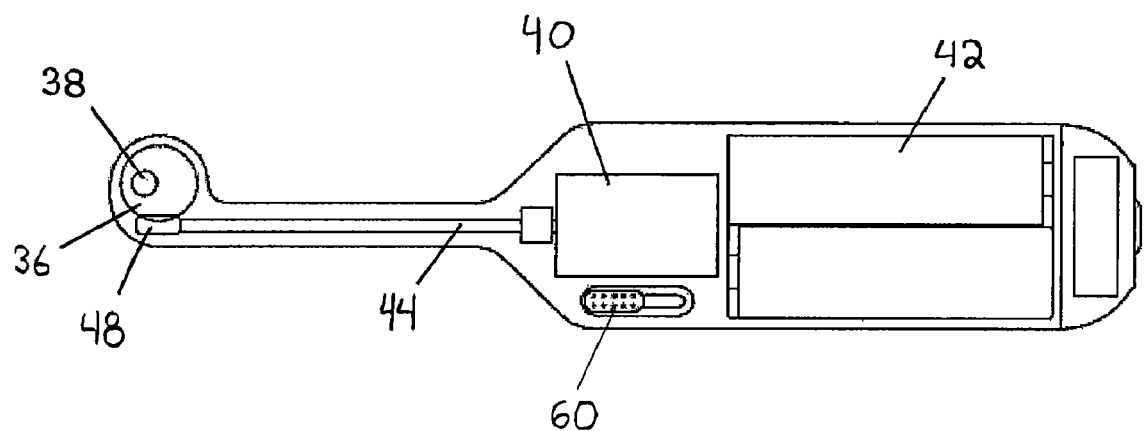
FIG. 8 illustrates a cross-sectional back view of an electric toothbrush.
Figure 9:
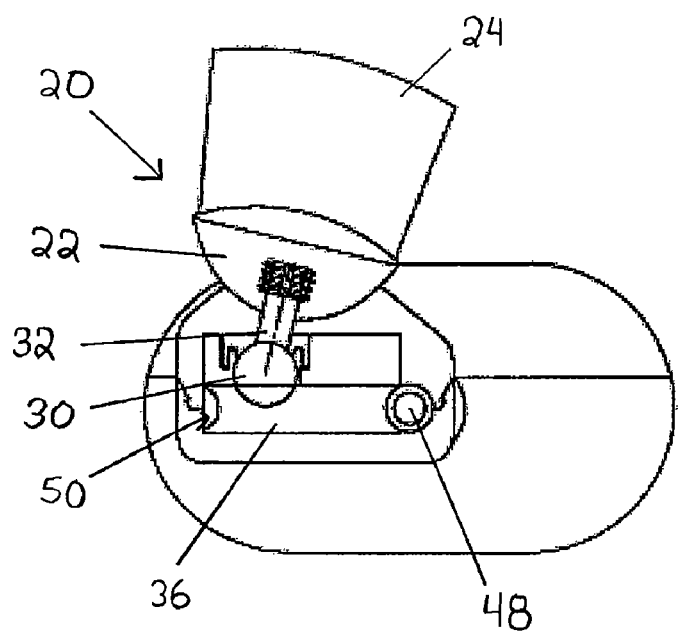
FIG. 9 illustrates a cross-sectional top view of an electric toothbrush.
Figure 10:
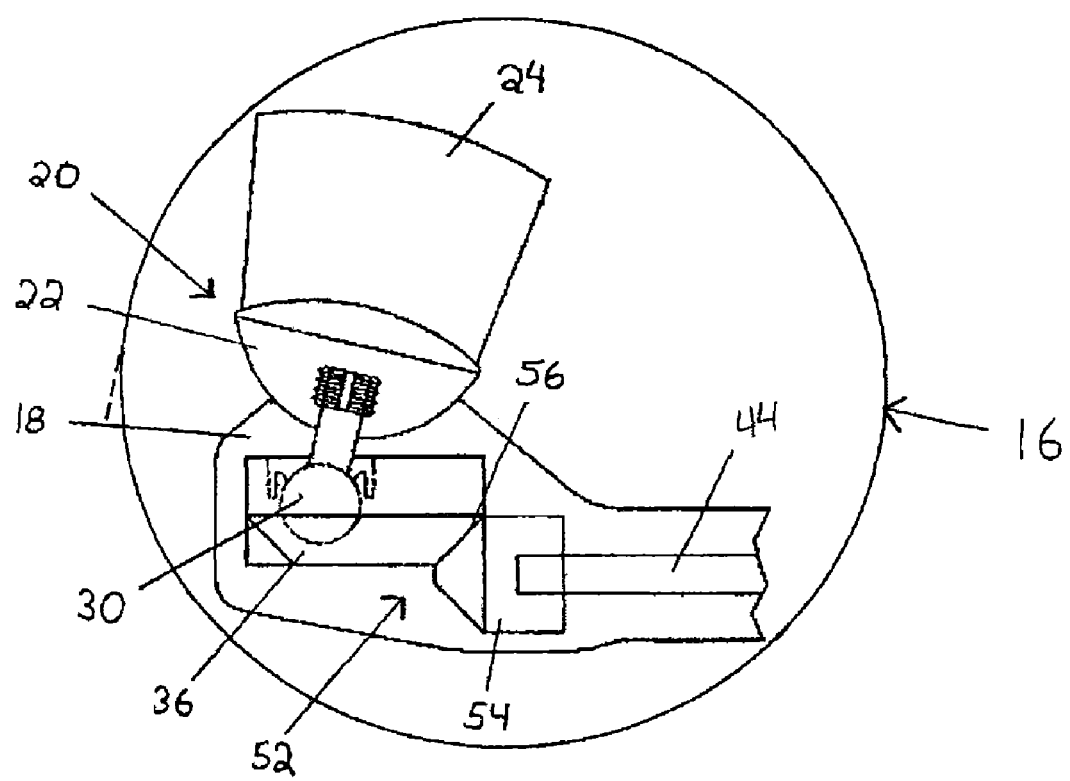
FIG. 10 illustrates a cross-sectional side view of an electric toothbrush having a bevel gear wheel engagement with an enhanced view of the toothbrush head.
Figure 11:
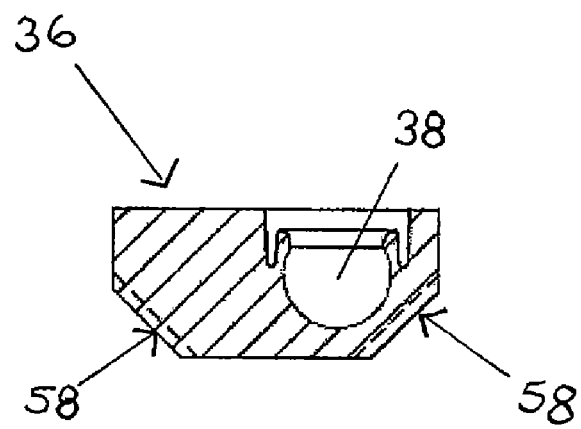
FIG. 11 illustrates a wheel having a beveled edge.
Figure 12:
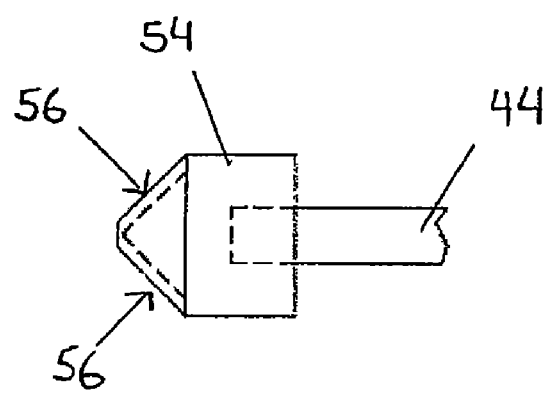
FIG. 12 illustrates a beveled member.

As illustrated in FIGS. 8 and 9, the brush head 20 may be positioned off-center of the motor 40 axis to accommodate the worm gear 46 coupling. The worm 46 may be generally aligned with the shaft 44 to rotate therewith. The wheel 36 may be positioned adjacent to the worm 48 in order for the worm 48 to engage the outer recessed portion 50 of the wheel 36. Thus, while the neck 14 and shaft 44 may extend along a central axis of the toothbrush 10, the wheel 36 and brush head 20 may be located away from the central axis, adjacent to the worm 48, to accommodate the worm gear 46 configuration.

In an alternative embodiment, the wheel 36 may be driven by a bevel gear 52 in place of the worm gear 46. The bevel gear 52 may operate substantially similar to the worm gear 46, but with a different coupling connection between the wheel 36 and the motor 40. As shown in FIGS. 10 through 14, the bevel gear 52 includes a beveled member 54 having an angled surface 56. The wheel 36 includes a similar angled surface 58. The beveled member 54 may include teeth or gears to engage similar teeth or gears on the angled surface of the wheel 36. As the motor 40 turns the shaft 44 and connected beveled member 54, the teeth of the beveled member 54 mesh with teeth of the wheel 36 to rotate the wheel 36 about its central axis. While the bevel gear 52 is described as utilizing gears and teeth to effectuate movement of the components, it will be appreciated that the bevel gear 52 may instead utilize a frictional engagement between the beveled member 54 and the wheel 36 to transfer rotational motion from the motor 40 to the wheel 36. Further, while the toothbrush 10 is described as including either a worm gear 46 or bevel gear 52 to transfer rotational power from the motor 40, it will be appreciated that the toothbrush 10 may utilize any coupling means between the motor 40 and the brush head.

Figure 13:
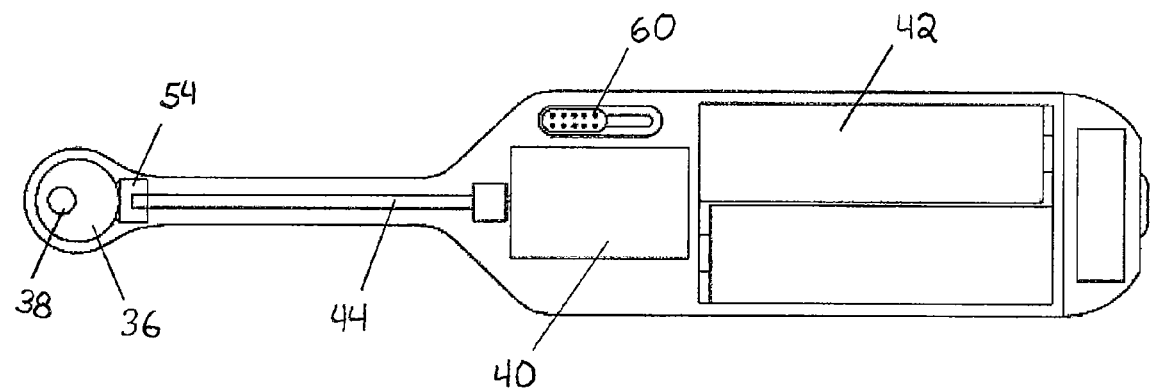
FIG. 13 illustrates a cross-sectional front view of an electric toothbrush having a bevel gear wheel engagement.
Figure 14:
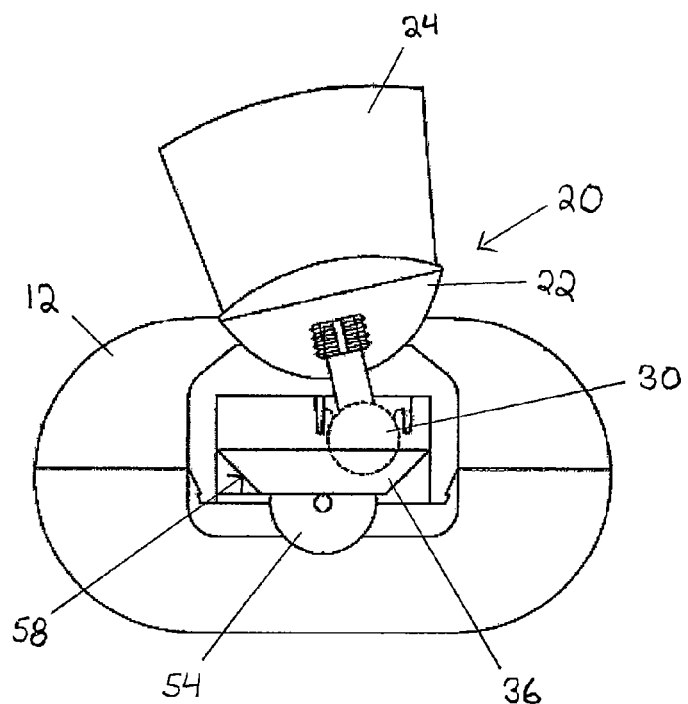
FIG. 14 illustrates a cross-sectional top view of an electric toothbrush having a bevel gear wheel engagement.

As illustrated in FIGS. 13 and 14, the bevel gear 52 configuration may allow the brush head 20 to be positioned in line with the motor 40. Similar to the worm 48, the beveled member 54 is generally aligned with the shaft 44 to rotate therewith. However, unlike the worm gear 46, which requires the wheel 36 to be positioned adjacent to the worm 48, the bevel gear 52 may allow the wheel 36 to be positioned above the beveled member 54.

The toothbrush 10 may include controls to regulate the movement of the brush head 20. For example, the toothbrush may include an on/off switch 60. The on/off switch 60 may toggle power to the motor as well as control the speed of the motor 40 between on and off. The on/off switch may be a sliding switch, as illustrated in FIGS. 8 and 13, or any other type of electric switch capable of toggling power to the motor 40. The toothbrush 10 may further include speed regulation controls (not shown). The speed regulation controls may allow a user to vary the rotational speed of the brush head 20.

Although the preferred embodiment of the present invention has been illustrated in the accompanying drawing and described in the foregoing detailed description, it is to be understood that the present invention is not to be limited to just the preferred embodiment disclosed, but that the invention described herein is capable of numerous rearrangements, modifications and substitutions without departing from the scope of the claims hereafter.

Having thus described the invention, we claim:

1. An electric toothbrush comprising:
a handle;
a neck connected to said handle;
a head connected to said neck, said head comprising:
  a base having a concave portion;
  a brush head having a convex portion, said convex portion of said brush head nesting within said concave portion of said base; and
  a plurality of bristles connected to said brush head;
a motor configured to drive the movement of said brush head;
a wheel coupled to said motor, wherein said brush head is coupled to said wheel; and
wherein said brush head is capable of rotational and tilting movement with respect to said base to provide three dimensional movement of said bristles.

2. The electric toothbrush of claim 1 further comprising a ball connected to the convex portion of said brush head, and a socket located in said wheel, wherein said socket is configured to receive said ball.

3. The electric toothbrush of claim 2, wherein said wheel is configured to rotate about it central axis.

4. The electric toothbrush of claim 3, wherein said socket is located a distance away from the central axis of said wheel.

5. The electric toothbrush of claim 4, wherein said ball is interconnected to said brush head by a barbed ball joint.

6. The electric toothbrush of claim 5, wherein said motor is coupled to said wheel by way of a worm gear.

7. The electric toothbrush of claim 6, wherein said worm gear includes a threaded worm connected to said motor, said threaded worm configured to engage a geared portion of said wheel.

8. The electric toothbrush of claim 5, wherein said motor is coupled to said wheel by way of a bevel gear.

9. The electric toothbrush of claim 8, wherein said bevel gear includes a beveled member connected to said motor, said beveled member configured to engage a beveled edge of said wheel.

10. The electric toothbrush of claim 9, wherein said beveled member includes teeth configured to mesh with tee of said beveled edge of said wheel.

11. An electric toothbrush comprising:
a handle;
a neck extending from said handle;
a head connected to said neck, said head comprising:
  a base having a concave portion;
  a brush head having a convex portion, said convex portion of said brush head nesting within said concave portion of said base; and
  a plurality of bristles connected to said brush head;
a motor connected to said brush head, said motor configured to drive said brush head in a rotational and tilting movement with respect to said base; and
a wheel coupled to said motor, wherein said brush head is coupled to said wheel.

12. The electric toothbrush of claim 11, wherein said motor is powered by batteries.

13. The electric toothbrush of claim 12, wherein said batteries are rechargeable batteries.

14. The electric toothbrush of claim 11 further comprising speed regulation controls configured to regulate the speed of the movement of said brush head with respect to said base.

15. An electric toothbrush head comprising:
a base having a concave portion;
a brush head having a convex portion, wherein said convex portion nests within said concave portion of said base;
a plurality of bristles connected to said brush head;
a driving mechanism connected to said brush head and configured to drive said brush head in a rotational and tilting motion relative to said base; and
wherein said driving mechanism is a wheel.

16. The electric toothbrush head of claim 15, wherein said brush head is connected to said wheel by a ball and socket joint.

17. The electric toothbrush head of claim 16, wherein said wheel is configured to be coupled to and driven by a motor.

* * * * *